Figure 1A:
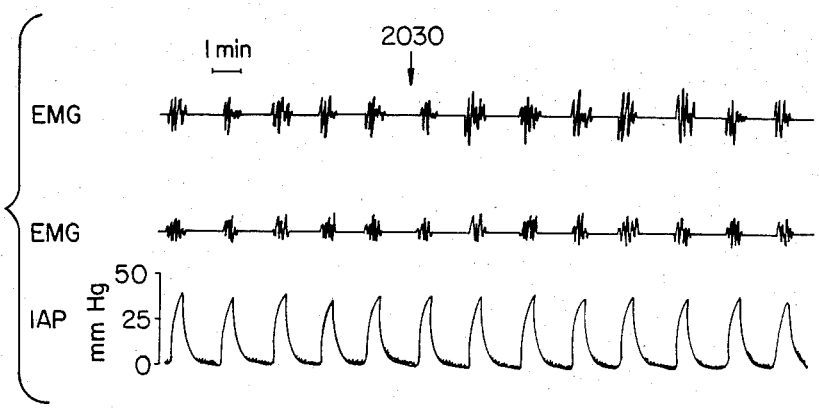

United States Patent [19]

Nathanielsz

[11] Patent Number: 4,500,523
[45] Date of Patent: Feb. 19, 1985

[54] SUPPRESSION OF PREMATURE LABOR BY USE OF AROMATASE INHIBITORS

[75] Inventor: Nathanielsz, Ithaca, N.Y.

[73] Assignee: Cornell Research Foundation, Inc., Ithaca, N.Y.

[21] Appl. No.: 597,876

[22] Filed: Apr. 9, 1984

Related U.S. Application Data

[63] Continuation-in-part of Ser. No. 475,576, Mar. 15, 1983, abandoned.

[51] Int. Cl.³ .............................................. A61K 31/56
[52] U.S. Cl. .................................................... 514/178
[58] Field of Search ........................................ 424/243

[56] References Cited

U.S. PATENT DOCUMENTS 4,235,893 11/1980 Brodie et al. ....................... 424/243

OTHER PUBLICATIONS

Brodie et al., *Steroids*, 38: 693–702 (1981).
Taylor et al., *Journal of Obstetrics and Gynecology*, 146, No. 5, pp. 557–567 (Jul. 1983).
Weiss et al., *Proceedings of the Society for Experimental Biology and Medicine*, 151, pp. 113–116 (1976).
Chemical Abstracts (1979) vol. 91 Par. 168,933 (J).
Chemical Abstracts (1982) vol. 97 Par. 120,724 (P).
Chemical Abstracts (1982) vol. 97 Par. 104,455 (T).

*Primary Examiner*—Elbert L. Roberts

[57] ABSTRACT

This invention relates to the use of aromatase inhibitors to suppress premature labor in mammals by administering an aromatase inhibitor preferably 4-hydroxy-4-androstene-3,17-dione or 4-acetoxy-4-androstene-3,17-dione to a pregnant mammal.

14 Claims, 1 Drawing Figure

SUPPRESSION OF PREMATURE LABOR BY USE OF AROMATASE INHIBITORS

This invention was made under and is subject to the terms and conditions of the United States Department of Health and Human Services grant number NIH-HD-17129.

CROSS-REFERENCE TO RELATED APPLICATION

This application is a continuation-in-part of application Ser. No. 475,576, filed Mar. 15, 1983, now abandoned.

BACKGROUND OF THE INVENTION

The myometrium contracts spontaneously throughout gestation. This activity has been confirmed experimentally in several species, including humans, by measuring increases in intra-amniotic pressure (IAP) or changes in myometrial electromyographic activity (EMG). Continuous IAP and EMG recordings in chronically catheterized sheep show the presence throughout most of gestation of "contractures," EMG events of long duration (5-7 min.) that produce a small increase in IAP. The duration of these contractures decreases, while the frequency increases, as labor approaches; Nathanielsz et al., *Am. J. Obstet. Gynecol.*, 138: 653 (1980); Krishnamurti et al., *J. Reprod. Fert.*, 64: 59 (1982).

In primates, short-term recordings of IAP in pregnant rhesus monkeys show the presence of episodes of increased IAP, and the frequency of these episodes seems to be higher in late gestation; (Corner et al., *Am. J. Obstet. Gynecol.*, 85: 179 (1963)). Continuous recording of IAP in chronically catheterized rhesus monkeys maintained in restraint chairs indicates that there is a circadian pattern of change of both the frequency and the rise of IAP generated in late gestation (Harbert, *Am. J. Obstet. Gynecol.*, 129: 401 (1977)). Discontinuous myometrial EMG recordings in cynamologous monkeys chronically implanted with electrodes also suggest the presence of circadian variation of the frequency of EMG signals, and a change in the duration of the signal throughout the day; (Germain et al., *Am. J. Obstet. Gynecolo*, 142: 513 (1982)). EMG recordings in pregnant humans have been limited to labor, or during induction of labor (Wolfs et al., *Acta. Obstet. Gynecol. Scand. (Suppl).*, 9, (1979)).

It has recently been discovered through the study of electromyographic activity (EMG) in pregnant rhesus monkeys that at least two types myometrial activity occur during pregnancy. One of these, named Type I and associated with labor and delivery, is characterized by frequent bursts (e.g., 10 to 45 per hour) of electrical activity that last from 0.5 to 1.2 minutes. The other type of EMG activity observed, named Type II, and associated with spontaneous myometrial contractions during the normal development non-labor and delivery stages of pregnancy, consists of fragmented series of discharges that last 2 to 15 minutes and occur up to six times an hour. The frequency of Type I EMG events when present generally show a circadian pattern of low amplitude with a maximum at night. This daily pattern is amplified during the 8-10 days preceding delivery.

Direct observation and manual analysis of polygraph tracings showed that EMG and IAP activity were always closely coordinated. There were no consistent differences between EMG recordings made at placental and extraplacental sites, nor between fundus and body of the uterus. The frequency of trains of potentials appeared to be proportional to IAP increase achieved, although this has not yet been subjected to rigorous quantitation. Combining EMG and IAP recordings show that activity formed distinct bursts.

Figure 1B:
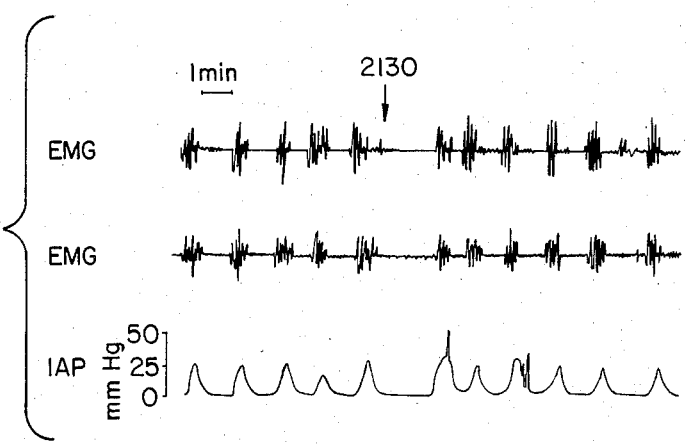

Two types of episodes were distinguished:

Type I (FIGS. 1A,B)—These were periods of continuous EMG discharges of 0.5-1.2 minutes duration associated with a symmetrical IAP peak. There were up to 45 events/hour. The frequency of biphasic action potentials, counted from records made at a paper speed of 5 mm/sec., was 106 to 196 spikes/min. Type I activity during labor (FIG. 1B) was indistinguishable from Type I activity at other stages of gestation (FIG. 1A).

Figure 1C:
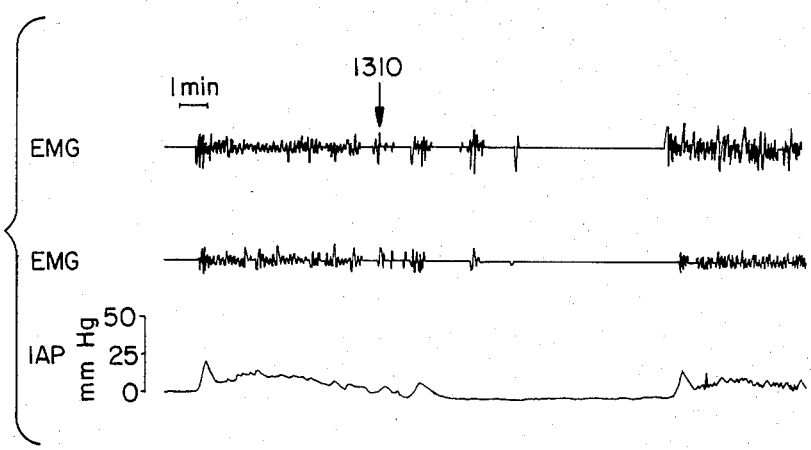

Type II (FIG. 1C)—These were a fragmented series of EMG discharges of 2-20 minutes duration associated with corresponding irregular IAP rises which remained above baseline for the duration of the event. The frequency of action potentials was similar to that in Type I at the beginning of each event, but ranged from 5 to 31 spikes/minute thereafter. There were up to 6 events/hour.

It is noted that 4-hydroxy-4-androstene-3,17-dione (4-OHA) and 4-acetoxy-4-androstene-3,17-dione (4-AcA) are taught in the art as aromatase inhibitors which reduce preovulatory ovarian estrogen secretion, inhibit ovulation and cause regression of hormone dependent mammary tumors in rats. They are also taught to inhibit peripheral aromatization in rhesus monkeys. It was also reported that 4-OHA and 4-AcA in the presence of NADPH, cause rapid, time-dependent loss of aromatase activity in microsomes isolated from human term placentae and ovaries from pregnant mares' serum gonadotropin primed rats; Brodie et al., *Steriods*, 38: 693 (1981).

It is pointed out that one of the few drugs presently available for the management of preterm labor, ritodrine (e.g. as the hydrochloride) appears to have serious potential side effects, and in addition, its efficacy is questioned by some authorities. There remains a clear need for other effective preterm labor management drugs.

DESCRIPTION OF THE INVENTION

It has now been discovered that aromatase (estrogen synthetase) inhibitors which retard enzyme activity in the placenta of mammals such as for example, sheep, monkeys and humans, are effective in terminating or moderating Type I myometrial activity and thus are useful in the prevention or management of preterm labor in pregnant mammals; including labor which occurs spontaneous with or subsequent to operative intervention on the pregnant uterus, such as corrective fetal surgery for example conducted to correct fetal and renal tract abnormalities or neurophysiological abnormalities, including hydrocephalus. The invention has application in agricultural, veterinary, as well as human clinical use. The current evidence of this utility is derived from studies in the non-human primate.

While any known placental aromatase inhibitor can be employed the presently preferred inhibitors are 4-hydroxy-4-androstene-3,17-dione (4-OHA) and 4-acetoxy-4-androstene-3,17-dione (4-AcA).

The amount of aromatase inhibitor is employed in a Type I myometrial contraction activity suppressing amount. For 4-OHA and 4-AcA, this amount is usually about 5 to about 500 milligrams and preferably between about 50 to 200 milligrams per day per kilogram of body weight of the pregnant female, preferably the total daily dose is administered in fractional doses for example, twice daily.

The aromatase is preferably administered orally, intraperitoneally, or intraveneously.

The aromatase can be formulated with pharmaceutically acceptable inert solvents, diluents or carriers to assist in administration and to provide appropriate dosage units. Useful formulating materials for intramuscular injection include arachis oil and peanut oil. The formulations can be employed which are similar to those currently employed for known related steroids.

It is noted that the aromatase inhibitors are useful to manage spontaneous premature labor as well as trauma and surgically induced Type I myometrial activity which could lead to premature labor, including Type I activity induced by uterine surgery. The aromatase can be employed in response to an apparent Type I myometrium episode or as a prophylactic against the occurrence of Type I myometrium activity in situations that precipitate or increase Type I activity, such as surgery, particularly uterine surgery.

The effect of the aromatase inhibitor appears to be dose response related and to be reversible upon cessation of administration. It is noted that a significant time elapses after administration before Type I activity is significantly suppressed (about 36 hours in monkeys with 4-OHA). Where the aromatase inhibitor is employed at or near term upon withdrawal of aromatase inhibitor use, Type I activity reoccurs at relatively reproducible time intervals on repeat administration.

Administration of aromatase inhibitor for more than 8 days in pregnant monkeys has not resulted in any signs of fetal compromise. On each instance the fetus survived the maternal administration of the drug and the fetal heart rate remained within normal limits.

EXAMPLES

Materials and Methods

Care of the Animals

Pregnant rhesus monkeys (*Macaca mulatta*) of known gestation age were employed. Gestation length for the colony from which these animals were obtained is 168±6 (mean±SD) days. They were housed in the room in which they were eventually studied for 4-6 weeks before surgery and given water and Purina Monkey Chow ad libitum, supplemented with fresh and dried fruit. Lights were left on daily for 12 hr beginning at 0700. The animals were conditioned to restraining chairs for 1-2 weeks before surgery.

Surgical Procedures

Food and water were withdrawn 20 hr prior to surgery. On the morning of surgery, 60 micrograms of glycopyrrollate and 100 mg Ketamine (Vetalar, Parke Davis and Co., Detroit, Mich. 48232) were administered intramuscularly. After tracheal intubation, anesthesia was induced with a mixture of 1.5% fluothane in oxygen and nitrous oxide, 400-600 cc/min. A maternal femoral artery and vein were exposed and siliconized Tygon catheters (0.04 inches o.d. and 0.03 inches i.d.) were threaded into the descending aorta and inferior vena cava for about 13 cm to lie at a level between the renal vessels and the bifurcation into the iliac vessels. The maternal abdomen was open by a vertical midline incision from the umbilicus to above the pubic symphysis. Uterine electromyographic (EMG) activity was recorded via electrode wires of vinyl insulated multistrand stainless steel (Cooner Wire Company, Chatsworth, Calif.). EMG electrodes were sutured into the uterine muscle 0.6-1 cm apart such that a bared portion (1-1.5 mm) remained buried (1). One pair was placed over a placental site, one at a distant site and an indifferent electrode at a site distant from these. Before closing the abdominal cavity, the peritoneum was irrigated with Kefzol (Cefazoline sodium, Eli Lilly Co., Indianapolis, Ind. 46285), 1 g in 20 ml saline.

The fascia of the rectus abdominis muscle was closed with interrupted 00 Dexon sutures. All catheters and electrodes were tunnelled under the skin to sites in the flank. The skin was closed with a subcuticular suture. After surgery the animal was placed in the restraining chair. This procedure did not cause any evident postural hypotension, as indicated by pallor, sweating and disorientation. Maternal catheters were kept patent by an infusion with heparinized saline (20 units/ml) at 0.1 ml/hr (fetus) and 0.2 ml/hr (mother). The antibiotics Gentamycin sulfate, 8 mg (Schering Pharmaceutical Co., Kenilworth, N.J. 07033) and Omnipen-N, 1 g (Wyeth Labs, Inc., Philadelphia, Pa. 19101) were administered i.m. twice daily for five days following surgery. No tocolytic medication was used in any of the animals.

Instrumentation

EMG were recorded on Beckman 16-channel recorders. EMG recordings were initiated immediately after surgery, and were then made continuously at a paper speed of 9 cm/hr. for the duration of the preparation. Maternal blood pressure and heart rate were intermittently measured. Fetal heart sounds were checked using a Doppler ultrasound stethescope.

4-OHA Formulation

The composition of the 4-OHA formulation administered intramuscularly to the monkeys below was:
150 milligrams 4-OHA sonicated in 2.0 ml of 0.3% hydroxypropyl cellulose.

Rhesus 7

Initial surgery was performed Day 1 (110 days gestation. Maternal aortic and inferior vena caval catheters and maternal uterine EMG leads were placed.

1st Administration of 4-OHA

Neither catheter worked after surgery, so on Day 7 surgery was conducted for recatheterization. At +9 days from the first surgery the mother pulled her arterial catheter out, had to be unchaired and taken to surgery for recatheterization at 11:30 am following a reasonably large bleed. Day 10—Type I activity appeared in both EMG leads when the lights went out at about 19:00 hours and lasted about 4 hours. The next night Type I began again and lasted 6 hours. By Day 13 the Type I's were now very active and lasted 6 hours. 150 mg of 4-OHA was administered intramuscularly (i.m.) on Day 14 at 13:40. Type I activity began at 19:00 hours and lasted about 5 hours. This was the fifth consecutive night of activity. 150 mg of 4-OHA was given i.m. at midnight. 150 mg of 4-OHA was given i.m. at 12:00 on Day 15. Fourth 150 mg dose Day 15 in the evening 11:38. No Type I activity on the night of Day 15. Type I activity did not come back the next few evenings. The last 150 mg 4-OHA dose was given at midnight between Day 15 and Day 16.

2nd Administration of 4-OHA

On the night of Day 23 at 19:00 hours (eight days after the drug was stopped) Type I activity returned and lasted about 6 hours. 4-OHA administration was begun again at noon on Day 24 at 13:15 hours. At about 19:00 hours Type I activity returned for 6 hours. On the night of Day 25 when 19:00 hours would have been 30 hours after the first dose of 4-OHA there was no Type I activity. The 4-OHA was given for 3 days 150 mg twice daily in total. The last dose was given at 20:00 hours on Day 26.

3rd Administration of 4-OHA

Since no catheters were flowing on Day 28 the monkey was taken back to surgery for catheterization of left femoral region. On Day 35, at 145 days gestation, Type I activity reappeared at night and lasted 4½ hours. 150 mg of 4-OHA was given the following morning and a second dose in the evening at 21:30. Type I activity occurred on the night of Day 36 for 5½ hours. Twice daily 150 mg doses of 4-OHA were continued and on the night of Day 37 there was no Type I activity. 4-OHA was administered twice a day until midnight between Day 39 and Day 40. Type I activity returned on the evening of Day 44 about 114 hours after the last dose was administered.

4th Administration of 4-OHA

On the night of Day 44 (153rd day of gestation) Type I activity lasted 4½ hours. Administration of 4-OHA was begun again and appears to be at least partially successful. Quantification using a computer is necessary to assess the exact degree of inhibition. A live female fetus was delivered by cesarian section at 163 days gestation. The newborn monkey survived, was hand reared and sent to a zoo.

Rhesus 9

Initial surgery at 106 days of gestation (Day 1). Maternal aortic and inferior vena caval catheters, uterine EMG wires. At 121 days, 15 days after the initial operation, uterine surgery was performed to place ultrasound crystals on the fetus. 150 mg of 4-OHA was given i.m. for one day before and for three days after the surgery and no Type I's were seen in the 8 days post surgery. In 17 previous pregnant animals in which the uterus had been opened at surgery, Type I activity was present in the days immediately after surgery. This Type I activity after surgery in the 17 control animals is attributed to the stress of surgery causing the release of androgens from the fetal and to some extent maternal adrenal with the subsequent aromatisation of these androgens to estrogens in the placenta. This stress should have been similar in Rhesus 9 to all the previous 17 uterine surgeries and the above described uterine surgery.

The last 150 mg i.m. dose of 4-OHA was given at 8:00 pm on Day 21 and although there was a considerable amount of myometrial activity, there was no Type I activity. Type I activity reappeared on Day 24 at about 5:00 pm and the delivery of the fetus occurred at 10:30 pm. Thus, Type I activity reappeared about 72 hours after cessation of drug administration. The fetus was in good condition and had apparently been alive shortly before the delivery. Death was due to a breach presentation.

In addition to the foregoing three further pregnant rhesus monkeys were operated on respectively at 116, 117 and 127 days gestation. 4-OHA was administered to the mothers for 36 hours before fetal surgery and for 3 days after surgery. No Type I contractions were observed in any of these operated animals.

I claim:

1. A method of suppression or managing premature labor in a pregnant female mammal which is undergoing or which has undergone fetal surgery, and is therefore susceptible to premature labor which method comprises:
administering a Type I myometrial contraction reducing amount of a placental aromatase inhibitor to said female mammal to thereby suppress or manage said premature labor.

2. A method as in claim 1 where the inhibitor is administered in response to apparent premature labor.

3. A method as in claim 1 where the inhibitor is administered as a prophylactic against premature labor.

4. A method as in claims 1, 2, or 3 where the inhibitor is administered intramuscularly.

5. A method as in claims 1, 2, or 3 where the inhibitor is administered orally.

6. A method as in claims 1, 2, or 3 where the inhibitor is administered in combination with a pharmaceutically accepted solvent, diluent or carrier.

7. A method as in claims 1, 2, or 3 where the aromatase inhibitor is selected from the group consisting of 4-hydroxy-4-androstene-3,17-dione and 4-acetoxy-4-androstene-3,17-dione.

8. A method of suppressing or managing premature labor in a pregnant female mammal which comprises:
administering a Type I myometrial contraction reducing amount of a placental aromatase inhibitor to a pregnant female mammal in or susceptible to premature labor, to thereby suppress or manage said premature labor.

9. A method as in claim 8 where the inhibitor is administered in response to apparent premature labor.

10. A method as in claim 8 where the inhibitor is administered as a prophylactic against premature labor.

11. A method as in claims 8, 9, or 10 where the inhibitor is administered intramuscularly.

12. A method as in claims 8, 9, or 10 where the inhibitor is administered orally.

13. A method as in claims 8, 9 or 10 where the inhibitor is administered in combination with a pharmaceutically accepted solvent, diluent or carrier.

14. A method as in claims 8, 9 or 10 where the aromatase inhibitor is selected from the group consisting of 4-hydroxy-4-androstene-3,17-dione and 4-acetoxy-4-androstene-3,17-dione.

* * * * *